US008058613B2

(12) United States Patent  (10) Patent No.: US 8,058,613 B2
Lou et al.  (45) Date of Patent: Nov. 15, 2011

(54) MICROMECHANICAL DEVICES FOR MATERIALS CHARACTERIZATION

(75) Inventors: Jun Lou, Houston, TX (US);
Yogeeswaran Ganesan, Houston, TX (US); Yang Lu, Houston, TX (US);
Cheng Peng, Houston, TX (US)

(73) Assignee: William Marsh Rice University, Houston, TX (US)

( * ) Notice: Subject to any disclaimer, the term of this patent is extended or adjusted under 35 U.S.C. 154(b) by 173 days.

(21) Appl. No.: 12/607,550

(22) Filed: Oct. 28, 2009

(65) Prior Publication Data
US 2010/0108884 A1    May 6, 2010

Related U.S. Application Data

(60) Provisional application No. 61/109,054, filed on Oct. 28, 2008.

(51) Int. Cl.
*G01N 23/225* (2006.01)
*G01N 3/42* (2006.01)
*G01N 3/48* (2006.01)
(52) U.S. Cl. ........... 250/310; 250/442.11; 73/78; 73/81; 73/82
(58) Field of Classification Search .................. 250/306, 250/307, 310, 442.11
See application file for complete search history.

(56) References Cited

U.S. PATENT DOCUMENTS

| | | | | |
|---|---|---|---|---|
| 5,157,831 A * | 10/1992 | Wang et al. | .................. | 29/876 |
| 6,590,212 B1 * | 7/2003 | Joseph et al. | .................. | 250/311 |
| 6,674,077 B1 * | 1/2004 | Joseph et al. | .................. | 250/311 |
| 7,183,548 B1 * | 2/2007 | Kley | .................. | 250/310 |
| 7,461,543 B2 * | 12/2008 | Degertekin | .................. | 73/105 |
| 7,514,680 B1 * | 4/2009 | Kley | .................. | 250/306 |
| 7,635,844 B2 * | 12/2009 | Joseph et al. | .................. | 250/310 |
| 7,858,936 B2 * | 12/2010 | Bray et al. | .................. | 250/307 |
| 2007/0045537 A1 * | 3/2007 | Joseph et al. | .................. | 250/310 |
| 2010/0279128 A1 * | 11/2010 | Lou et al. | .................. | 428/457 |

OTHER PUBLICATIONS

Yu, et al., "Strength and Breaking Mechanism of Multiwalled Carbon Nanotubes Under Tensile Load", Science, 287:2000, pp. 637-640.
Zhu, et al., "An electromechanical material testing system for in situ electron microscopy and applications", Proc. Nat. Acad. Sci., 102:2005, pp. 14503-14508.

* cited by examiner

*Primary Examiner* — Bernard E Souw
(74) *Attorney, Agent, or Firm* — Winstead PC

(57) ABSTRACT

The present disclosure describes micromechanical devices and methods for using such devices for characterizing a material's strength. The micromechanical devices include an anchor pad, a top shuttle platform, a nanoindenter in movable contact with the top shuttle platform and at least two sample stage shuttles. The nanoindenter applies a compression force to the top shuttle platform, and the at least two sample stage shuttles move apart in response to the compression force. Each of the at least two sample stage shuttles is connected to the top shuttle platform and to the anchor pad by at least one inclined beam. Methods for using the devices include connecting a sample between the at least two sample stage shuttles and applying a compression force to the top shuttle platform. Application of the compression force to the top shuttle platform results in a tensile force being applied to the sample. Measuring a tip displacement of the nanoindenter is correlated with the sample's strength. Illustrative materials that can be studied using the micromechanical devices include, for example, nanotubes, nanowires, nanorings, nanocomposites and protein fibrils.

27 Claims, 13 Drawing Sheets

MICROMECHANICAL DEVICES FOR MATERIALS CHARACTERIZATION

CROSS REFERENCE TO RELATED APPLICATIONS

This application claims priority to U.S. provisional patent application 61/109,054, filed Oct. 28, 2008, which is incorporated by reference herein in its entirety.

STATEMENT REGARDING FEDERALLY SPONSORED RESEARCH

This invention was made with government support under Grant Number ECCS 0702766 awarded by the National Science Foundation and Grant Number FA8650-07-2-5061, awarded by the U.S. Department of Defense. The Government has certain rights in the invention.

BACKGROUND

The mechanical and electrical properties of nanomaterials such as, for example, nanotubes, nanowires and nanorings, have led to intense interest in these materials. Potential applications for these nanomaterials include miniaturized electronic, optical, thermal and electromechanical systems. Many of these nanomaterial applications further rely upon the superior strength of the nanomaterials. Deformation and failure of nanomaterials under mechanical load is of particular importance in structural applications such as, for example, composite systems and load carrying components in electromechanical systems. Therefore, a thorough understanding of the mechanical properties of individual nanomaterials is desirable, since there may be property differences observed for individual nanomaterials compared those observed in a bulk sample.

Many methods for mechanical characterization of individual nanomaterials are presently known in the art. The majority of these techniques employ electro-mechanical or thermo-mechanical coupling. Testing methods for real-time observation of individual nanomaterials under stress include, for example, resonance-based methods, microelectromechanical systems (MEMS)-based tensile testing using electrostatically- and thermally-actuated platforms, atomic force microscope (AFM)-assisted bending, and compression and tension tests. A number of the aforementioned techniques are either indirect (e.g., resonance based testing) or direct but qualitative (e.g., AFM-assisted bending). Furthermore, a significant drawback of known direct measurement techniques is that sample load and deformation cannot be simultaneously and independently measured in a quantitative manner. Electrostatically- and thermally-actuated platforms have been able to overcome some of the aforementioned limitations, but their implementation is both expensive and challenging.

In view of the foregoing, new devices and methods for direct measurement of the mechanical properties of nanomaterials would be of considerable benefit in the art. In particular, such new devices and methods would desirably incorporate capabilities for simultaneous observation and mechanical testing of the nanomaterials under load.

SUMMARY

In various embodiments, micromechanical devices for characterizing a material's strength are described herein. The devices include an anchor pad, a top shuttle platform, a nanoindenter in movable contact with the top shuttle platform and at least two sample stage shuttles. The nanoindenter applies a compression force to the top shuttle platform. Each of the at least two sample stage shuttles is connected to the top shuttle platform by at least one inclined beam. Each of the at least two sample stage shuttles is connected to the anchor pad by at least one inclined beam. The at least two sample stage shuttles move apart from one another in response to the compression force.

In various embodiments, methods for measuring a sample's strength are described herein. The methods include providing a device for characterizing a material's strength, as described in accordance with the various embodiments herein; connecting a sample between the at least two sample stage shuttles; applying a compression force to the top shuttle platform with the nanoindenter; and measuring a tip displacement of the nanoindenter.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
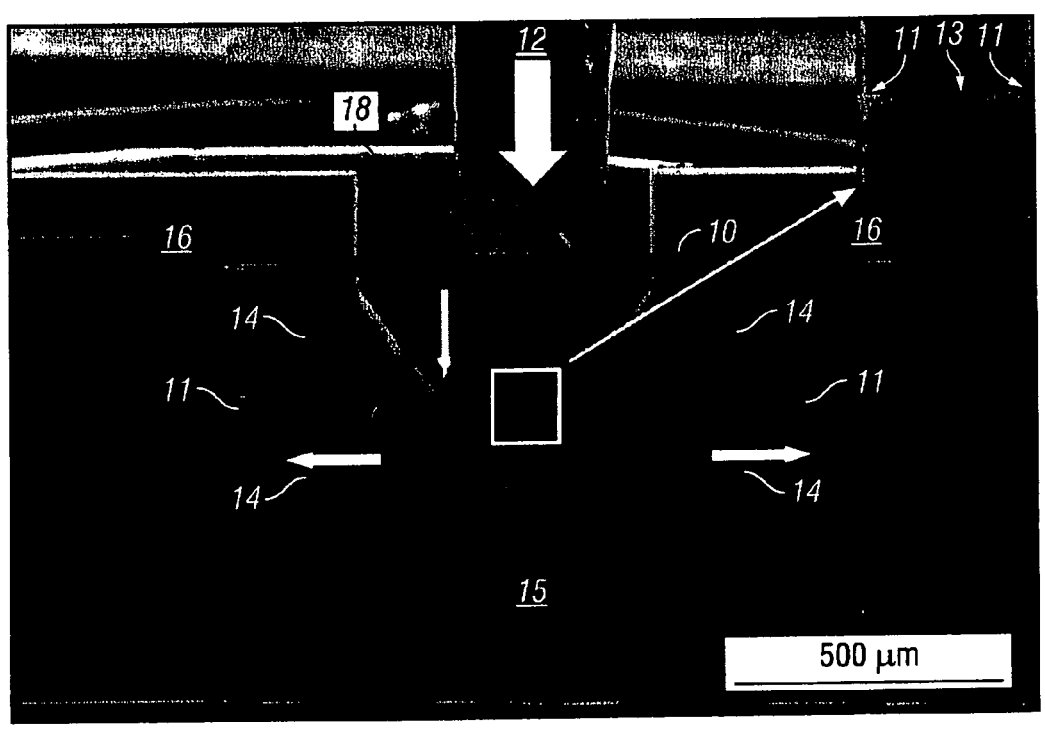
FIG. 1 shows an illustrative SEM image of a micromechanical device embodiment for characterizing a sample's strength.

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

In various embodiments, micromechanical devices and methods for characterizing mechanical properties of materials using such devices are described in the present disclosure. The devices and methods of the present disclosure advantageously allow measurement of a sample's strength to be made though direct application of a tensile force to the sample. The tensile force applied to the sample directly results from application of a compression force to the micromechanical devices described herein. The devices of the present disclosure are mechanical systems, as opposed to existing devices and methods that involve electro-mechanical or thermo-mechanical coupling to measure mechanical properties. The simple mechanical design of the device advantageously leads to few sources of error and high resolution measurement of the mechanical properties.

High resolution measurement of mechanical properties using the devices of the present disclosure is made possible by using a nanoindenter to apply a compression force to the devices. Application of a compression force from the nanoindenter results in a 'push-pull' actuation of the devices to deliver a tensile load to the sample. In other words, application of a compression force (push) to the devices results in delivery of a tensile load (pull) to the sample. Further, the devices are designed such that the sample can be simultaneously observed while under a tensile load. The high resolution measurement of force and displacement offered by nanoindenters (nano-Newton and nanometer resolution, respectively) allows the devices of the present disclosure to provide their high resolution measurement of the mechanical properties.

In various embodiments, micromechanical devices for characterizing a material's strength are described herein. The devices include an anchor pad, a top shuttle platform, a nanoindenter in movable contact with the top shuttle platform and at least two sample stage shuttles. The nanoindenter applies a compression force to the top shuttle platform. Each of the at least two sample stage shuttles is connected to the top shuttle platform by at least one inclined beam. Each of the at least two sample stage shuttles is connected to the anchor pad by at least one inclined beam. The at least two sample stage shuttles move apart from one another in response to the compression force.

FIG. 1 presents an illustrative SEM image of an embodiment of a micromechanical device 1 for characterizing a sample's strength. Fabrication of such a device is given as an experimental example herein. As shown in FIG. 1, the device includes a top shuttle platform 10 and two sample stage shuttles 11. Nanoindenter 12 is in movable contact with top shuttle platform 10. Nanoindenter 12 applies a compression force to top shuttle platform 10. In turn, the compression force generated by nanoindenter 12 results in movement of the sample stage shuttles 11 apart from one another. Sample 13 is connected between the two sample stage shuttles 11 as shown in the inset, and a tensile force is applied to sample 13 when the sample stage shuttles 11 move apart. Relative motion of the various parts of device 1 are represented by the block arrows in FIG. 1.

Referring still to FIG. 1, device 1 also includes inclined beams 14 connecting the sample stage shuttles 11 to the top shuttle platform 10 and connecting the sample stage shuttles 11 to anchor pad 15. Top shuttle platform 10 is also connected to anchor pad 15 through lateral support beams 16. The number of inclined beams 14 and the angle that they make with the sample stage shuttles 11 are but one of several parameters that determine overall stiffness of the devices.

Figure 2C:
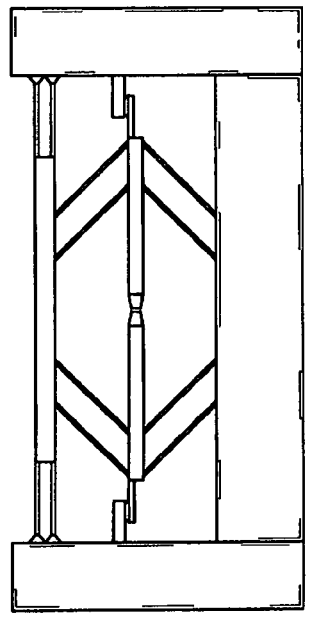
FIGS. 2A through 2D show schematic illustrations of illustrative alternative embodiments of the device of FIG. 1 in which the number of inclined beams and the angle that they make with the sample stage shuttles are varied.
Figure 2D:
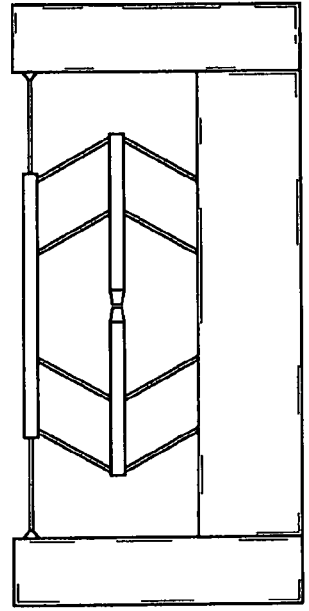
Figure 2A:
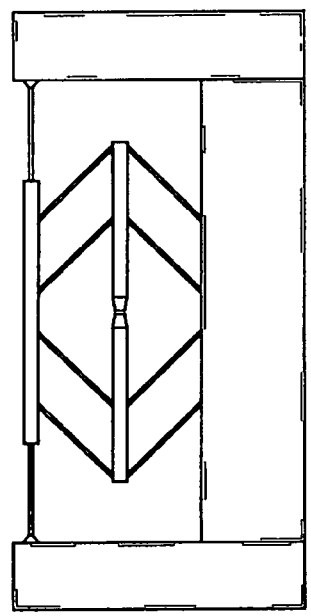
Figure 2B:
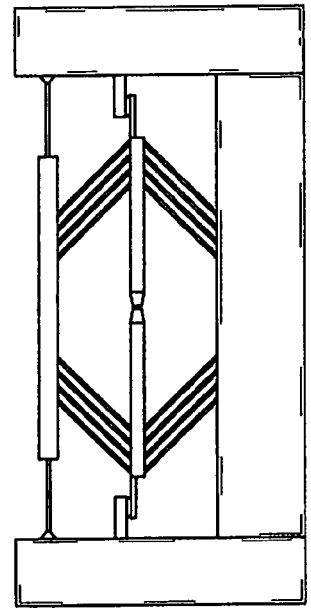

FIGS. 2A through 2D show schematic illustrations of illustrative alternative embodiments of the device of FIG. 1 in which the number of inclined beams and the angle that they make with the sample stage shuttles are varied. In FIGS. 2A through 2D, the nanoindenter has been omitted for clarity. FIG. 2A is a schematic illustration of the device of FIG. 1. The device of FIG. 2B includes additional inclined beams relative to the device of FIG. 2A, resulting in an increased stiffness of the device of FIG. 2B. The device of FIG. 2C has its inclined beams contacting the sample stage shuttles at a higher angle than the device of FIG. 2A, resulting in an increased stiffness in the device of FIG. 2C, even though the two devices have the same numbers of inclined beams. The device of FIG. 2D is stronger still than the devices of either FIG. 2A or 2C, since its inclined beams contact the sample stage shuttles at an even higher angle.

As described hereinabove, in various embodiments, the stiffness of the device is adjustable. In some embodiments, the stiffness is adjusted by modifying at least one device parameter including, for example, the thickness of the device, the number of inclined beams, and the angle at which the inclined beams contact the at least two sample stage shuttles. Accordingly, the stiffness of the device can be adjusted to accommodate testing of a wide range of materials having variable strengths.

In general, the number and positioning of the inclined beams is such that the devices are symmetrical and have two planes of symmetry bisecting the devices. In some embodiments, there are equal numbers of inclined beams on each sample stage shuttle. In some embodiments, there are equal numbers of inclined beams connecting each sample stage shuttle to the top shuttle platform and to the anchor pad. In other embodiments, there are unequal numbers of inclined beams connecting each sample stage shuttle to the top shuttle platform and to the anchor pad. In some embodiments, each inclined beam contacts the sample stage shuttles at the same angle. In other embodiments, at least one of the inclined beams contacts the sample stage shuttles at an angle that is different than that of any other of the inclined beams.

One of ordinary skill in the art will recognize that some embodiments of the devices may include asymmetrical positioning of the inclined beams. Such asymmetrical positioning of the inclined beams lies within the spirit and scope of the present disclosure. Asymmetrical positioning of the inclined beams may include, for example, placing different numbers of inclined beams at various points of the devices, placing the inclined beams at more than one angle where they contact the at least two sample stage shuttles, fabricating the inclined beams in variable thicknesses, and combinations thereof. In some embodiments of the devices, asymmetrical positioning of the inclined beams is such that there is no plane of symmetry bisecting the device. In other embodiments of the devices, asymmetrical positioning of the inclined beams is such that there is a plane of symmetry bisecting the device. In still other embodiments of the devices, asymmetrical positioning of the inclined beams is such that there are two planes of symmetry bisecting the device.

Referring again to FIG. 1, application of a compression force to the top shuttle platform 10 using nanoindenter 12 along a perpendicular axis of device 1 results in transformation of the compression force into two-dimensional linear motion of the sample stage shuttles 11. Such linear motion applies a tensile force to a sample 13 placed between sample stage shuttles 11. Transfer of load and motion is facilitated by inclined beams 14. Aligning nanoindenter 12 in the center of top shuttle platform 10 results in the sample stage shuttles 11 moving symmetrically away from one another and ensures that a sample clamped between the two sample stage shuttles 11 is exposed to a purely tensile force. Sample load is calculated using the known applied force and displacement data from the nanoindenter, after applying conversion factors calculated through finite element modeling.

In various embodiments, devices of the present disclosure also include a viewing means for observing a material in the device while the compression force is being applied (i.e., while the sample is undergoing tensile deformation). For example, such viewing means can include an optical microscope, a scanning electron microscope (SEM) or a transmission electron microscope (TEM). In some embodiments, the viewing means is an optical microscope. In other embodiments, the viewing means is a scanning electron microscope. In still other embodiments, the viewing means is a transmission electron microscope. As one of ordinary skill in the art will recognize, SEM and TEM experiments are performed under high vacuum conditions, whereas experiments with an optical microscope may be carried out under any pressure conditions ranging from high vacuum to ambient pressure. The ability of the devices to function under a variety of pressure conditions attests to the operational flexibility of the devices. Further, the ability of the devices to operate at ambient pressure allows tensile testing to be performed on nanomaterial samples dispersed in a solution.

Figure 3A:
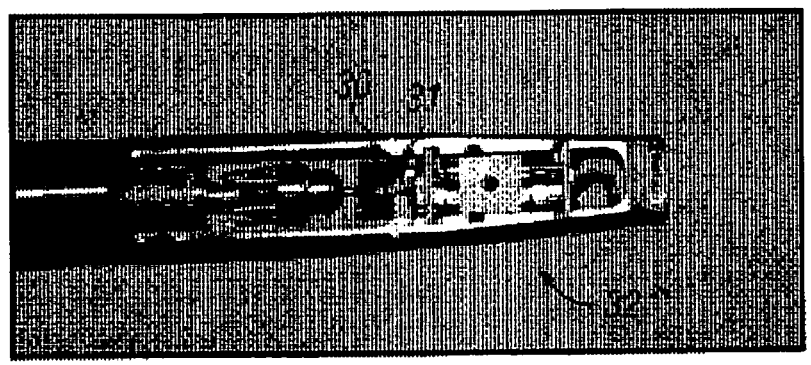
FIGS. 3A-3B show images of an illustrative micromechanical device of the present disclosure mounted on to a TEM stage.
Figure 3B:
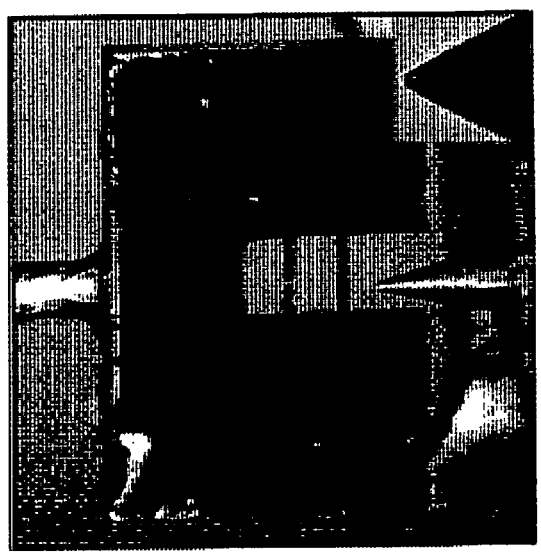
Figure 4:
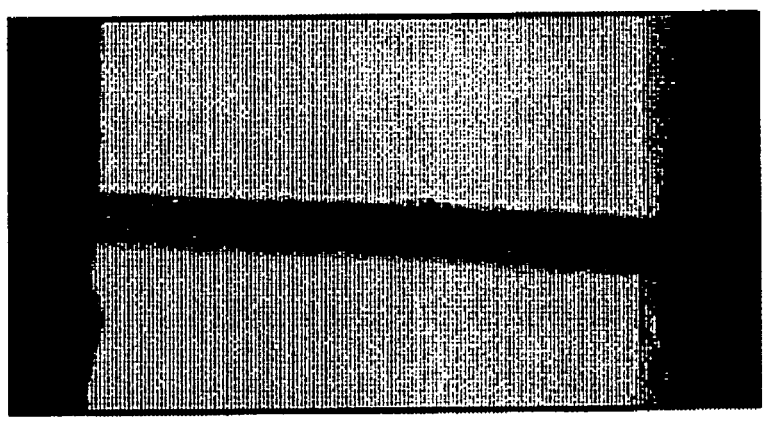
FIG. 4 shows an illustrative TEM image of a nickel nanowire sample mounted on the sample stage shuttles of a micromechanical device of the present disclosure.

Although many of the experimental examples referenced herein have utilized an SEM as the viewing means, the devices may be conveniently inserted on to a TEM stage to achieve even higher resolution measurements. FIGS. 3A-3B show images of an illustrative micromechanical device of the present disclosure mounted on to a TEM stage. For example, as shown in FIG. 3A, device 30 comprising nanoindenter 31 is mounted on to TEM stage 32. FIG. 3B shows an expanded view of device 30 and nanoindenter 31. FIG. 4 shows an illustrative TEM image of a nickel nanowire sample mounted on the sample stage shuttles of a micromechanical device of the present disclosure.

In some embodiments, the devices further include a viewing window that is substantially transparent to the viewing means. For example, the viewing window may be transparent toward visible light in an optical microscope or toward an electron beam in a TEM. Referring again to FIG. 1, a viewing window 18 is shown such that nanoindenter 12 and sample 13 are visible. In particular, the viewing window 18 may be used for viewing the sample 13 while under tensile load and to facilitate positioning of the head of nanoindenter 12. Fabrication of devices both with and without viewing windows is considered in more detail hereinbelow.

The opportunity to simultaneously view a material while it is under tensile load is a particular advantage of the devices of the present disclosure. Such simultaneous viewing can be useful for correlating observable sample deformation to the amount of tensile load being applied to the sample via the nanoindenter. For example, sample failure due to tensile load can be directly observed with the viewing means through the viewing window. In some embodiments, the viewing window is transparent to electrons so that viewing of the sample may be conducted with an electron beam, such as those used in TEM. In other various embodiments, the viewing window is transparent to at least one type of electromagnetic radiation such as, for example, visible radiation, ultraviolet radiation, infrared radiation, X-ray radiation, gamma rays and combinations thereof. For example, when observation of the sample is conducted visibly, the viewing window is transparent to at least visible radiation. In still other various embodiments, the viewing window is transparent to particle radiation such as, for example, electrons, protons, neutrons, positrons and combinations thereof. Scattering of particle radiation may be another useful way of observing changes that occur in the sample while it is under tensile load.

The type of nanoindenter used in the various embodiments of the devices and methods described herein is not particularly critical. In some embodiments, the nanoindenter is a quantitative nanoindenter. In some embodiments, the nanoindenter includes a blunt cube corner nanoindenter tip. Other various embodiments of nanoindenters suitable for use in the devices and methods of the present disclosure include, but are not limited to, a round end cone nanoindenter, a filament rod nanoindenter, a Berkovich nanoindenter, a Vickers nanoindenter, and a Knoop nanoindenter. Nanoindenter tips may be, for example, pyramidal, wedge-shaped, cone-shaped, cylindrical, spherical, or filament-like. In the experimental examples referenced herein, an INSEM® nanoindenter having a blunt cube corner nanoindenter tip was used. Positional resolution of such nanoindenters can be as precise as ±0.1 nm.

In various embodiments of the present disclosure, the top shuttle platform moves vertically in response to application of the compression force by the nanoindenter. In some embodiments, the devices of the present disclosure may be modified to eliminate or minimize vertical movement of the top shuttle platform during compression force application by the nanoindenter. Elimination or minimization of vertical movement is advantageous for maintaining nanoindenter alignment and focus of the viewing means on the sample. In various embodiments, elimination or minimization of vertical movement may be accomplished by adding additional inclined beams to induce a cascade amplification of the nanoindenter displacement.

Materials useful for making the devices of the present disclosure include, for example, silicon and silicon-on-insulator (SOI). The devices may be constructed on such materials using standard lithographic patterning, etching and masking techniques known to those of ordinary skill in the art. SOI is particularly advantageous for embodiments of the devices having viewing windows for observation of the sample material. Fabrication of such a device having a viewing windows is set forth hereinbelow as an experimental examples.

Figure 5:
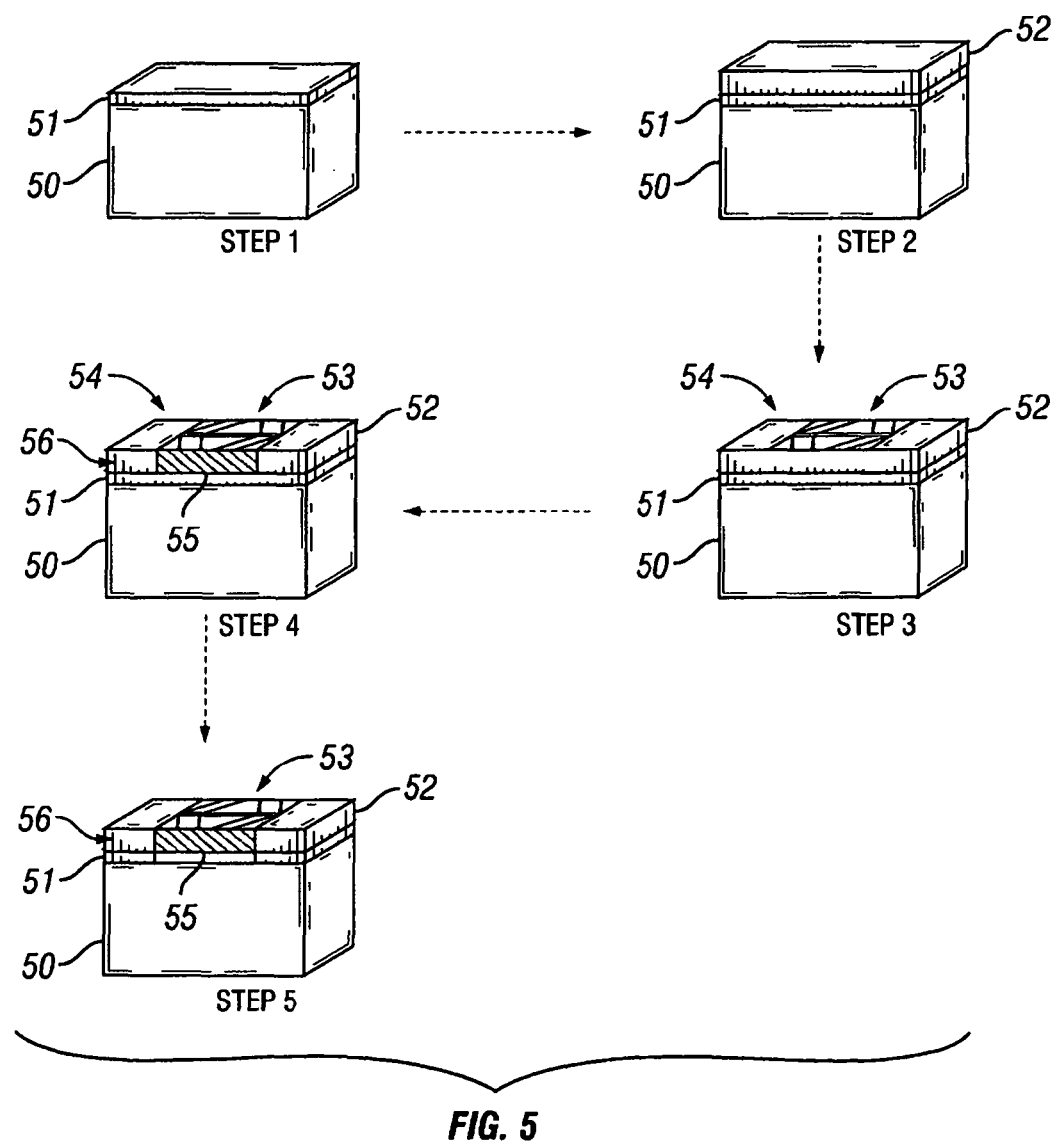
FIG. 5 shows a schematic of a non-limiting process by which micromechanical devices of the present disclosure may be fabricated from a silicon wafer.

FIG. 5 shows a schematic of a non-limiting process by which micromechanical devices of the present disclosure may be fabricated from a silicon wafer. The process includes: 1) depositing a silicon oxide layer 51 on silicon wafer 50, followed by annealing; 2) depositing a polysilicon layer 52 (for example, by chemical vapor deposition, CVD) on the silicon oxide layer 51, followed by annealing; 3) photolithographic patterning of device 53 on the top face 54 of polysilicon layer 52; 4) etching of polysilicon layer 52 by deep reactive ion etching; and 5) releasing device 53 by etching of silicon oxide layer 51 with hydrofluoric acid vapors, followed by drying using liquid carbon dioxide. Shaded region 55 on the front face 56 of polysilicon layer 52 ultimately becomes the top shuttle platform of device 53 where the nanoindenter applies the compression force.

Figure 6:
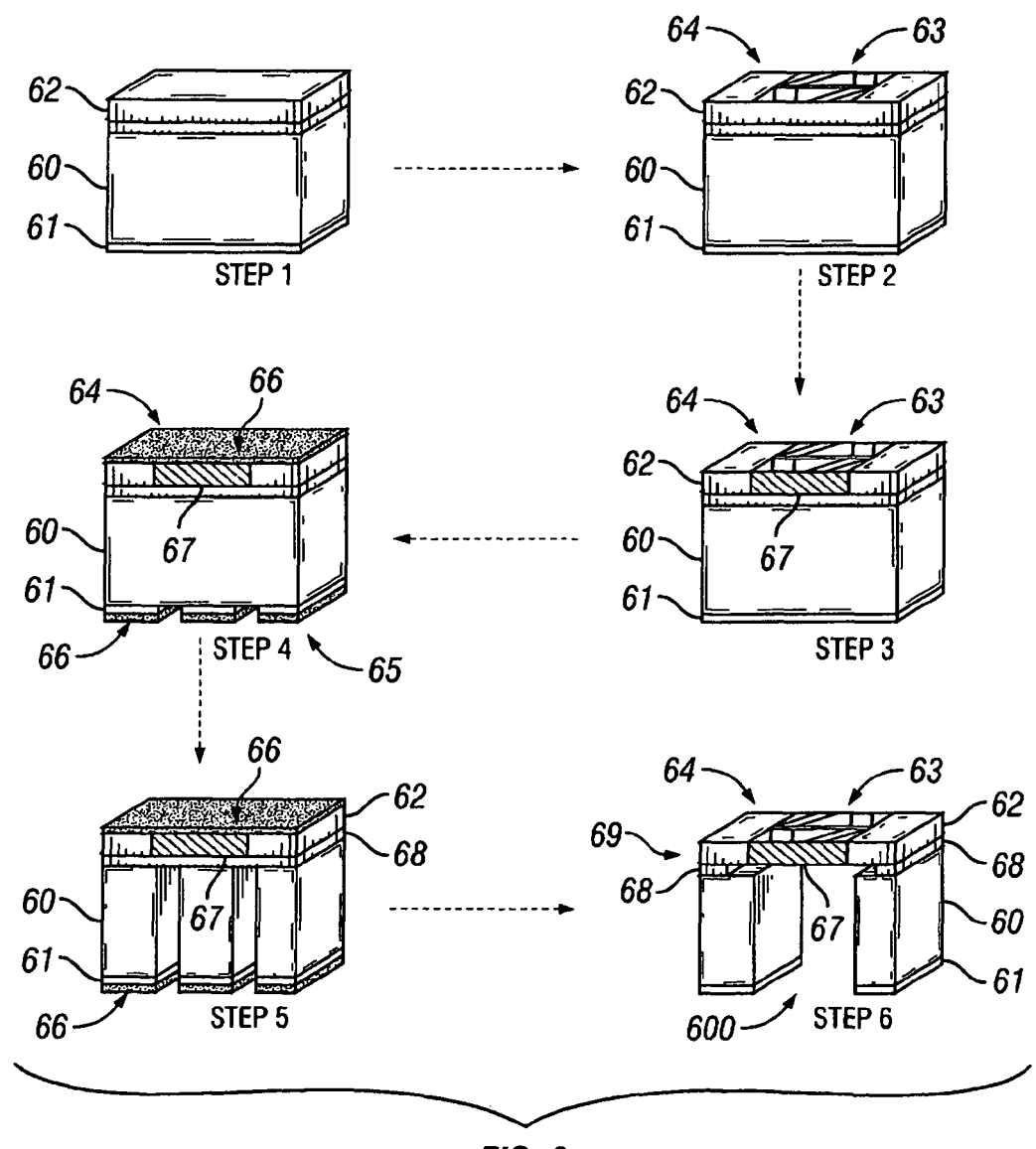
FIG. 6 shows a schematic of a non-limiting process by which micromechanical devices having a viewing window may be fabricated from SOI.

FIG. 6 shows a schematic of a non-limiting process by which micromechanical devices having a viewing window may be fabricated from SOI. The process includes: 1) performing a backside deposition (for example, by plasma enhanced CVD) of a silicon oxide layer 61 on silicon layer 60; 2) photolithographic patterning of device 63 on top face 64 of silicon layer 62; 3) etching of silicon layer 62 by deep reactive ion etching; 4) masking top face 64 and device 63 with a photoresist 66 and patterning backside 65 using photolithography, followed by backside oxide etching with hydrofluoric acid or buffered oxide etch (BOE) to remove a portion of silicon oxide layer 61; 5) etching silicon layer 60 using deep reactive ion etching; and 6) photoresist removal and device 63 release through etching of buried oxide layer 68 with hydrofluoric acid vapors. Shaded region 67 on the front face 69 of silicon layer 62 ultimately becomes the top shuttle platform of device 63 where the nanoindenter applies the compression force. The embodiment of FIG. 6 differs from that of FIG. 5 in that a portion of silicon layer 60 has been removed to define a viewing window 600 observable from the backside of device 63.

Finite Element Modeling (FEM). In order to derive the stress vs. strain curves from nanoindenter tip load vs. displacement data, three parameters are calculated by FEM. These parameters are: 1) the ratio of the applied load and the displacement of the nanoindenter tip (i.e., the system stiffness), defined herein as $K_S$; 2) the ratio of the force acting on the sample and the applied load of the nanoindenter tip (i.e., the force conversion coefficient), defined herein as $C_F$; and 3) the ratio of the sample stage shuttle displacement/sample elongation and the nanoindenter tip displacement (i.e., the displacement conversion coefficient), defined herein as $C_D$. One of ordinary skill in the art will recognize the meanings of these terms in the context of characterizing mechanical properties of materials.

Figure 7A:
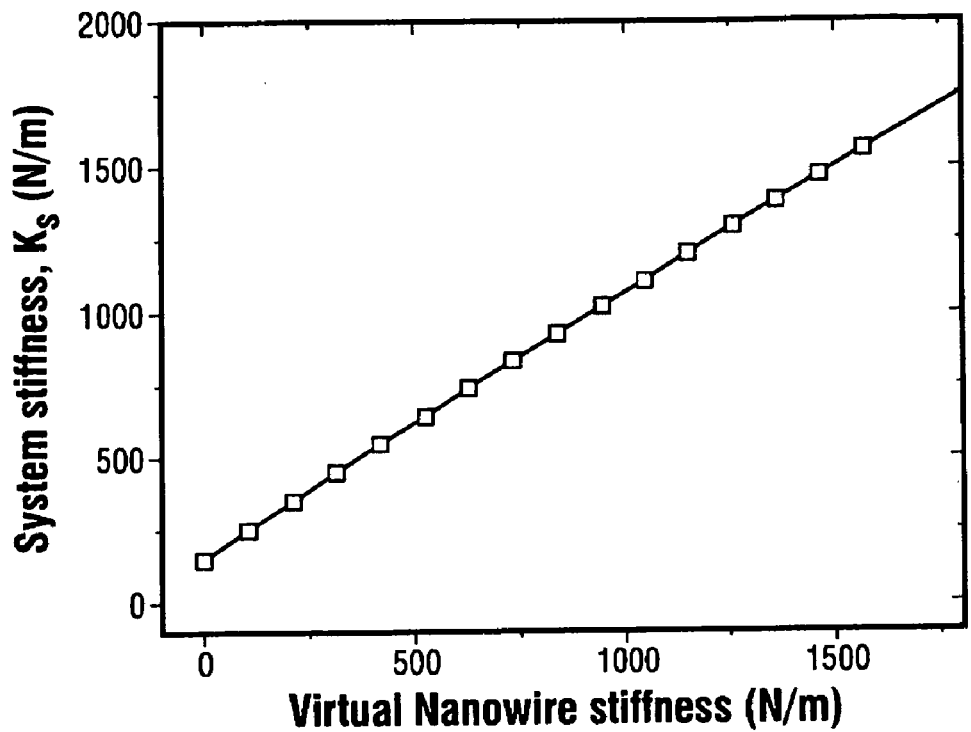
FIG. 7A shows an illustrative plot of system stiffness versus virtual nanowire stiffness.
Figure 7B:
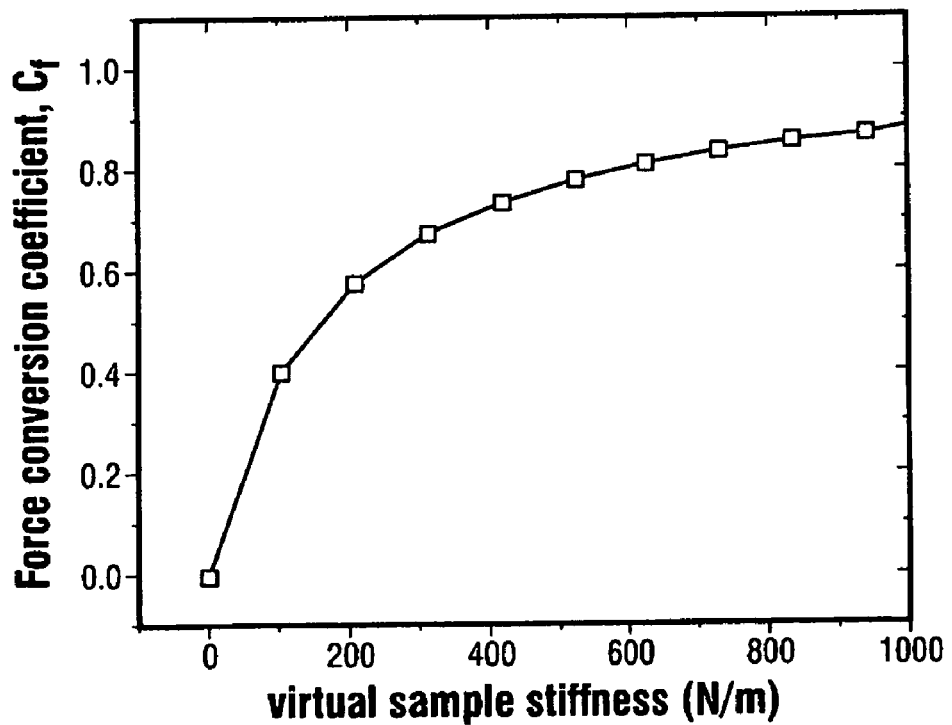
FIG. 7B shows an illustrative plot of force conversion coefficient versus virtual nanowire stiffness.
Figure 7C:
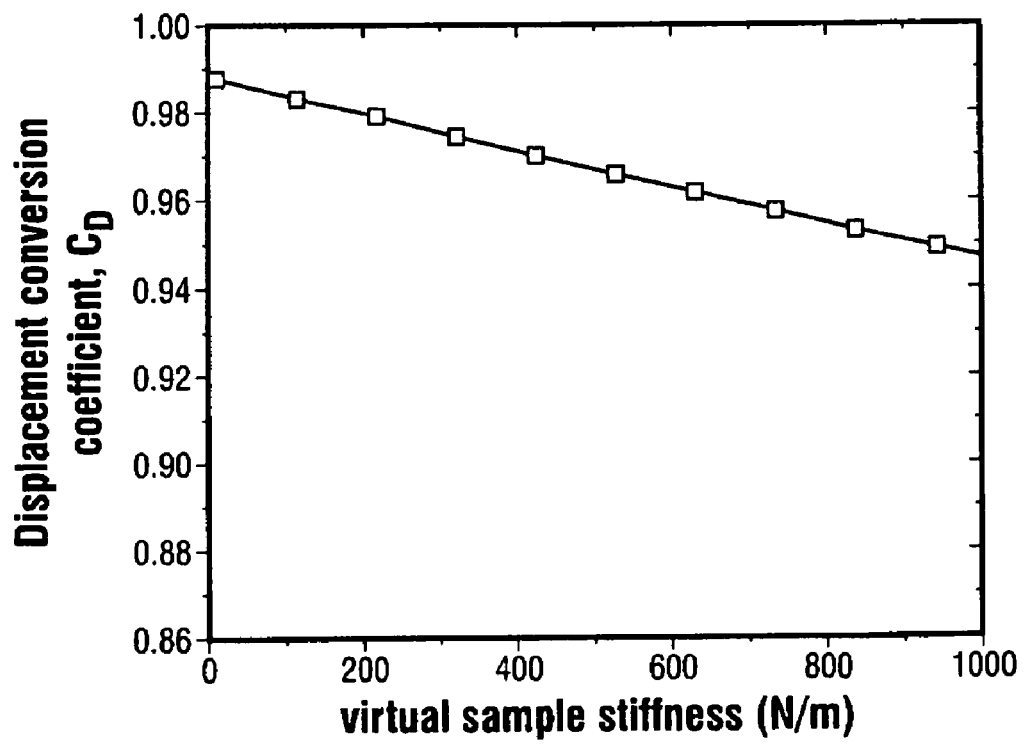
FIG. 7C shows an illustrative plot of displacement conversion coefficient versus virtual nanowire stiffness.

The details regarding FEM and associated testing of the devices described herein are set forth in (Y. Lu, et al., "A Multi-Step Method for In Situ Mechanical Characterization of 1-D Nanostructures Using a Novel Micromechanical Device," *Exp. Mech.*, in press: DOI 10.1007/s11340-009-922-0), which is incorporated herein by reference in its entirety. The FEM described herein includes three basic steps. First, a finite element model for the device clamped with a virtual nanowire sample is made. A series of virtual experiments are subsequently conducted using this model in order to obtain a system stiffness ($K_S$) vs. virtual nanowire stiffness curve. FIG. 7A presents an illustrative plot of system stiffness versus virtual nanowire stiffness. Next, FEM is used to obtain a plot of force conversion coefficient ($C_F$) vs. virtual nanowire stiffness. FIG. 7B presents an illustrative plot of force conversion coefficient versus virtual nanowire stiffness. A plot of the displacement conversion coefficient ($C_D$) vs. virtual nanowire stiffness is also obtained. FIG. 7C presents an illustrative plot of displacement conversion coefficient versus virtual nanowire stiffness. For all FEM analyses presented herein, the Young's modulus and Poisson's ratio of single crystal silicon (<100> orientation) were taken to be 160 GPa (value obtained via nanoindentation) and 0.278, respectively. The Poisson's ratio of the virtual nanowire was taken to be 0.310.

Error Analysis. The methods and devices described herein may be used to ascertain the value for the Young's modulus (E) of a material using Formula (1).

$$E = \frac{\sigma}{\varepsilon} = \frac{F_x/A}{\Delta L/L} = \frac{C_F F_y L}{C_D y_1 A} \quad (1)$$

In Formula (1), $C_F$ and $C_D$ are defined hereinabove, $F_y$ is the force applied by the nanoindenter, $y_1$ is the displacement of the top shuttle platform (assumed to be equal to the displacement of the nanoindenter head) in the sample's elastic regime, and L and A are the sample's length and cross-sectional area, respectively. Accordingly, the uncertainty in the determination of the value of E is given by Formula (2).

$$(\Delta E)^2 = \left(\frac{\partial E}{\partial C_F}\right)^2 (\Delta C_F)^2 + \left(\frac{\partial E}{\partial C_D}\right)^2 (\Delta C_D)^2 + \left(\frac{\partial E}{\partial F_y}\right)^2 (\Delta F_y)^2 + \quad (2)$$

$$\left(\frac{\partial E}{\partial y_1}\right)^2 (\Delta y_1)^2 + \left(\frac{\partial E}{\partial L}\right)^2 (\Delta L)^2 + \left(\frac{\partial E}{\partial A}\right)^2 (\Delta A)^2$$

$$= E^2 \left(\left(\frac{\Delta C_F}{C_F}\right)^2 + \left(\frac{\Delta C_D}{C_D}\right)^2 + \left(\frac{\Delta F_y}{F_y}\right)^2 + \right.$$

$$\left. \left(\frac{\Delta y_1}{y_1}\right)^2 + \left(\frac{\Delta L}{L}\right)^2 + \left(\frac{\Delta A}{A}\right)^2 \right)$$

The relative uncertainty in the value of E is accordingly given by Formula (3).

$$\left|\frac{\Delta E}{E}\right| = \sqrt{\left(\frac{\Delta C_F}{C_F}\right)^2 + \left(\frac{\Delta C_D}{C_D}\right)^2 + \left(\frac{\Delta F_y}{F_y}\right)^2 + \left(\frac{\Delta y_1}{y_1}\right)^2 + \left(\frac{\Delta L}{L}\right)^2 + \left(\frac{\Delta A}{A}\right)^2} \quad (3)$$

Since $C_F$ and $C_D$ are invariant parameters, $\Delta C_F$ and $\Delta C_D$ are equal to zero, which leads to simplification of Formula (3).

The uncertainty in the measurement of force $F_y$ and displacement $y_1$ is primarily due to limitations in the precision of the nanoindenter. For the INSEM® nanoindenter used in the various experimental examples described herein, the resolution of the force (load) and displacement values are ±50 nN ($\Delta F_y$) and ±50 nm ($\Delta y_1$), respectively. Since the maximum force ($F_y$) applied by the nanoindenter and the maximum displacement ($y_1$) of the top shuttle platform (equivalent to nanoindenter head displacement), are ~8 mN and ~25 µm, respectively, the relative errors of $F_y$ and $y_1$ are given by Formulas (4) and (5), respectively.

$$\left(\frac{\Delta F_y}{F_y}\right)^2 = \left(\frac{50 \text{ nN}}{8 \text{ mN}}\right)^2 < 0.01\% \tag{4}$$

$$\left(\frac{\Delta y_1}{y_1}\right)^2 = \left(\frac{50 \text{ nm}}{25 \text{ µm}}\right)^2 < 0.01\% \tag{5}$$

For observation of a sample in an SEM, uncertainty in the measurement of the sample's length (L) and diameter (D) arises from the pixel resolution of the SEM micrograph, which is approximately ±10 nm ($\Delta L$ and $\Delta D$). Since the length and diameter of the present samples are on the order of 10 µm and 350 nm, respectively, the relative errors of L and A are given by Formulas (6) and (7).

$$\left(\frac{\Delta L}{L}\right)^2 = \left(\frac{10 \text{ nm}}{10 \text{ µm}}\right)^2 < 0.01\% \tag{6}$$

$$\left(\frac{\Delta A}{A}\right)^2 = \left(\frac{2\Delta d}{d}\right)^2 = \left(\frac{2*10 \text{ nm}}{350 \text{ nm}}\right)^2 = 0.33\% \tag{7}$$

Combining the values from Formulas (4) through (7) into Formula (3) gives a relative uncertainty (error) of about 6% in the measurement of the sample's Young's modulus. As demonstrated above, the primary source of error lies in the measurement of sample's cross-sectional area.

In various embodiments, methods for measuring a sample's strength are described herein. The methods include providing a device for characterizing a material's strength, as described in accordance with the various embodiments herein; connecting a sample between the at least two sample stage shuttles; applying a compression force to the top shuttle platform with the nanoindenter; and measuring a tip displacement of the nanoindenter. The tip displacement correlates with the sample's strength.

In various embodiments, the connecting step of the methods includes attaching the sample to the at least two sample stage shuttles with epoxy. Other means for attachment lie within the spirit and scope of the present disclosure and are within the capabilities of one of ordinary skill in the art. Alternative means include, for example, welding, brazing and gluing. In some embodiments, samples may also be attached through electrostatic or magnetic means.

In some embodiments, the methods of the present disclosure further include placing the device on the stage of a microscope. In various embodiments, the microscope may be a scanning electron microscope or a transmission electron microscope. In other various embodiments of the methods, the microscope may be an optical microscope. In further embodiments, the methods also include observing the sample with the microscope while a compression force is being applied to the sample. In some embodiments, particularly those conducted in a scanning electron microscope or transmission electron microscope, the observing step is conducted with an electron beam.

In some embodiments of the methods of the present disclosure, the sample is suspended in a liquid phase. The devices of the present disclosure are advantageous in their flexibility to be operated with both solid samples and samples contained in a liquid phase. In some embodiments of the methods, the devices are immersed in a liquid during their actuation. The ability to perform measurements while the devices are immersed in a liquid phase is of particular utility for measuring mechanical properties of, for example, biological specimens and like samples that are not otherwise stable when removed from solution. Such biological specimens include, for example, DNA and protein fibrils. In embodiments wherein a liquid sample is being assayed, the device is placed in an optical microscope to avoid evaporating the liquid in the high-vacuum environment of an SEM or TEM.

In some embodiments, the devices and methods described herein can be used to perform fiber pullout testing from nanocomposites. For example, a sample of a nanocomposite containing nanowires or nanotubes in a polymer matrix can be placed in the devices and connected to the sample stage shuttles. Thereafter, the force required for nanowire or nanotube pullout may be determined. In addition, the devices can be used for nanoscale fatigue and creep testing, further attesting to the utility and operational flexibility of the devices.

EXPERIMENTAL EXAMPLES

The following examples are provided to more fully illustrate some of the embodiments disclosed hereinabove. It should be appreciated by those of skill in the art that the techniques disclosed in the examples that follow represent techniques that constitute illustrative modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

Example 1

Fabrication of an Illustrative Device from a Silicon-on-Insulator Wafer

Micromechanical devices were prepared from a SOI wafer according to the following two-mask procedure. A schematic illustration of this process was previously set forth in FIG. 6. Device layers formed from Si<100> and having a thickness of either 9.5±0.5 µm, 9.0±0.5 µm or 6.0±0.5 µm were constructed on the SOI surface. The SOI also included a 2 mm or 5 mm thick buried oxide (BOX) layer beneath the device layer and a 490±10 µm thick Si layer as a handle layer for supporting the devices.

A 4 µm thick silicon oxide film was first grown on the backside of the SOI wafer by plasma enhanced chemical vapor deposition (PECVD) at 340° C. with $SiH_4$ and $O_2$ gases acting as the precursors. Standard photolithography techniques were then employed and a dry etching step, within a PlasmaTherm SLR-770 Inductively Coupled Plasma Reactive Ion Etcher (Plasma-Therm, St. Petersburg, Fla.) using the Bosch recipe, was performed in order to pattern devices on the front side of the wafers. Photolithographic techniques were again used to pattern dicing lines and windows on a resist layer coated on the back side of the wafer. Mask alignment, during this step, was performed using a SUSS Micro-Tec MA6 Mask Aligner (SUSS MicroTec AG, Garching, Germany) equipped with front to back alignment capability. The silicon oxide layer on the back side of the wafer was then etched in a buffered oxide etch (BOE, 10:1 $H_2O$:HF) solution. Before the sample was immersed in the BOE solution, the front side of the wafer was coated with a thick photoresist layer in order to protect the exposed buried oxide layer. The silicon handle layer was subsequently dry etched with a deep reactive ion etcher. The thick photoresist layer on the front side was subsequently removed using acetone. Devices were then released by placing the wafers in a hydrofluoric acid vapor tank for a specific amount of time. The duration of the release step was long enough for the movable portions of the device to be completely released while some of the oxide remained beneath the anchor pads leaving them attached to the silicon handle layer. The released devices were then placed in a methanol bath and subsequently dried within a supercritical drier (Tousimis research corporation, Rockville, Md.) using liquid carbon dioxide (in order to avoid stiction issues) before individual device isolation.

Example 2

Connecting Ni Nanowires to the Devices

A portion of each sample stage shuttle in the device was coated with a thin layer of epoxy (HARDMAN Water-Clear Epoxy). A droplet from a nickel nanowire solution (containing <112> oriented Ni nanowires grown via electrodeposition; ~10-~30 μm long and ~200-~400 nm in diameter), was first dispersed in isoproponal by ultrasonication for 5-10 minutes. A drop of this dispersion was then deposited on top of a silicon wafer coated with a 5 nm thick layer of gold. Individual nanowires (~15 μm long and 200-300 nm in diameter; visible under an optical microscope) were picked up from the surface of the silicon wafer and placed across the sample stage shuttles using micromanipulators housed within a probe station (The Micromanipulator Co., Carson City, Nev.). The epoxy layer, upon hardening, clamped the Ni nanowire sample to the sample stage shuttles for tensile strength evaluation. The distance between clamping points was determined to be 3.59 μm and 3.62 μm for two samples prepared in accordance with the above procedure, as determined using SEM.

Example 3

Device Testing Procedures for Ni Nanowires

The two clamped Ni nanowires of Example 2 were tested in accordance with the procedures described in Example 3 below. For the testing described below, 9 μm thick devices having 8 inclined beams (2 beams per sample stage shuttle attached to the anchor pad and 2 beams per sample stage shuttle attached to the top shuttle platform; see FIGS. 1 and 2A) were used. The inclined beams were attached to the sample stage shuttles at a 45 degree angle.

Tensile testing of the clamped Ni nanowires was performed within an SEM (FEI Quanta 400 high resolution field emission scanning electron microscope, FEI company, Hillsboro, Oreg.) equipped with an INSEM® nanoindenter (Agilent Technologies, Oak Ridge, Tenn.) system. A blunt cube corner nanoindenter tip was used to perform the indentation. The nanoindenter tip was first aligned with the device's top shuttle platform to ensure that the sample stage shuttles moved symmetrically. Alignment was facilitated using markers that had been previously incorporated into the device design. Once alignment was completed, the electron beam of the SEM was focused on the Ni nanowire sample in order to monitor its deformation as a function of tensile load, while the load was being applied. Indentation of the top shuttle platform was performed with the nanoindenter in the load controlled mode with the loading rate being held at a constant value of 40 μN/s.

The maximum load applied to the Ni nanowire sample using the nanoindenter was 2 mN. Once the maximum load value was reached, the load was held constant for 0.5 seconds, and unloading was thereafter conducted at the same rate. A thermal drift correction hold step was performed at $1/10^{th}$ the maximum applied load for about 50 seconds in order to account for small amounts of thermal expansion or contraction in the test material and/or indentation equipment.

Figure 8:
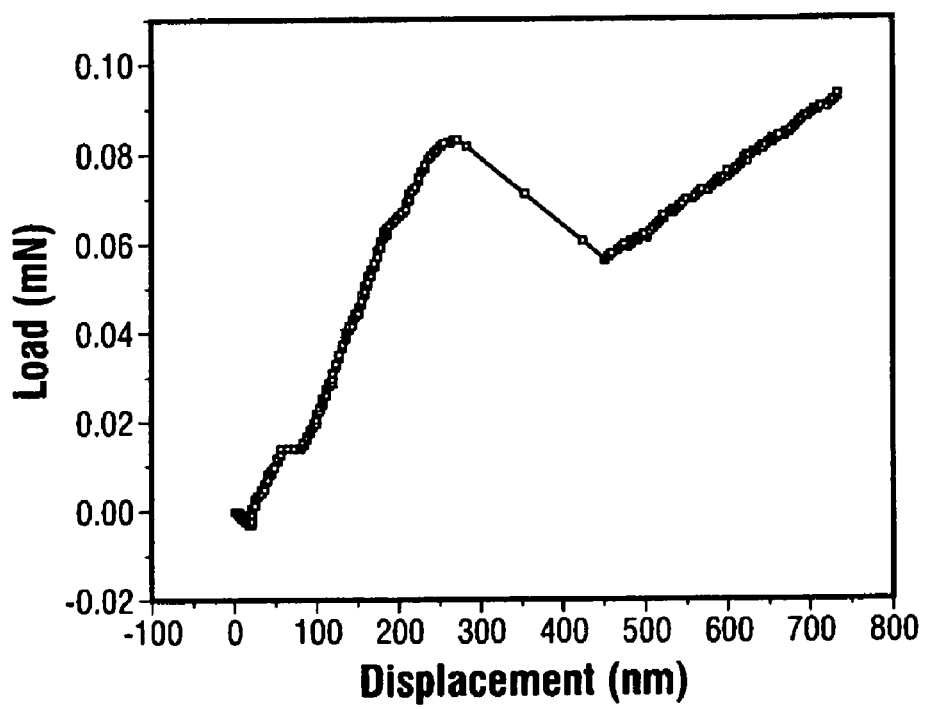
FIG. 8 shows an illustrative plot of nanoindenter load versus displacement for tensile measurement of a Ni nanowire sample.
Figure 9A:
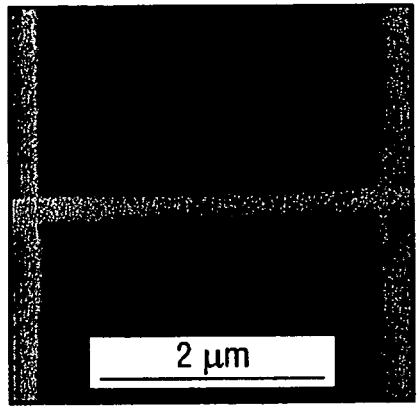
FIGS. 9A-9F show illustrative time-lapse SEM images of a Ni nanowire mounted to the micromechanical device (t=0 s; t=1 s; t=2 s; t=3 s, t=5 s and t=16 s, respectively), which were obtained while a load was being applied.
Figure 9B:
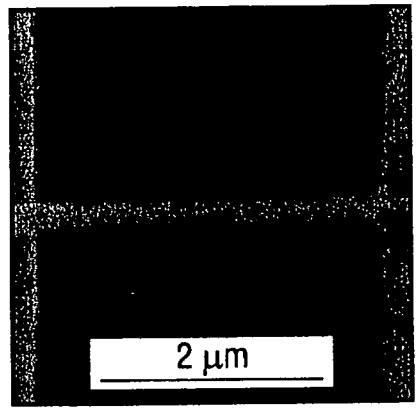
Figure 9C:
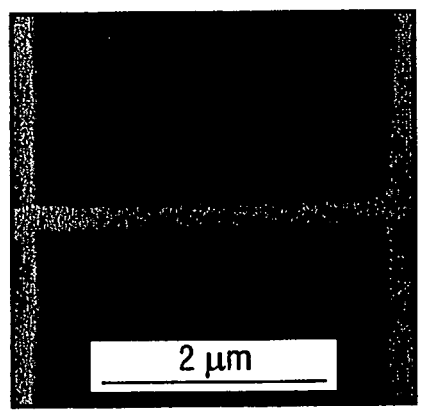
Figure 9D:
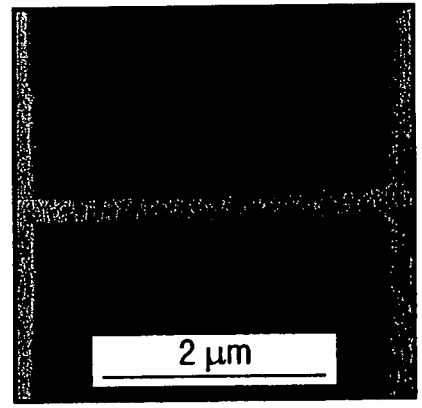
Figure 9E:
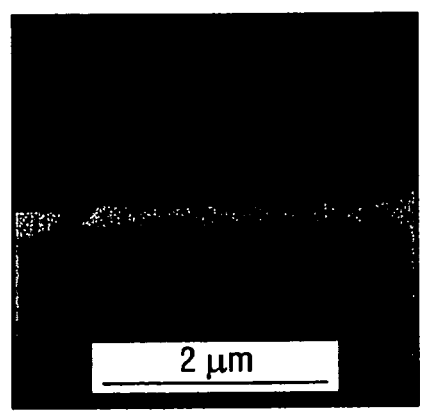
Figure 9F:
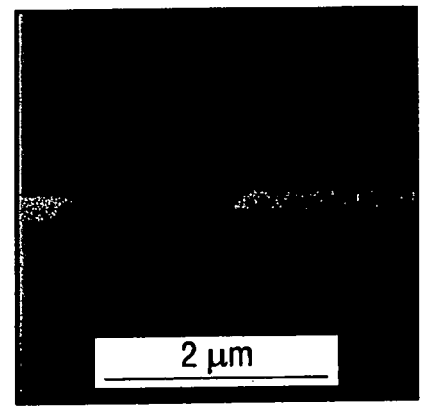
Figure 10:
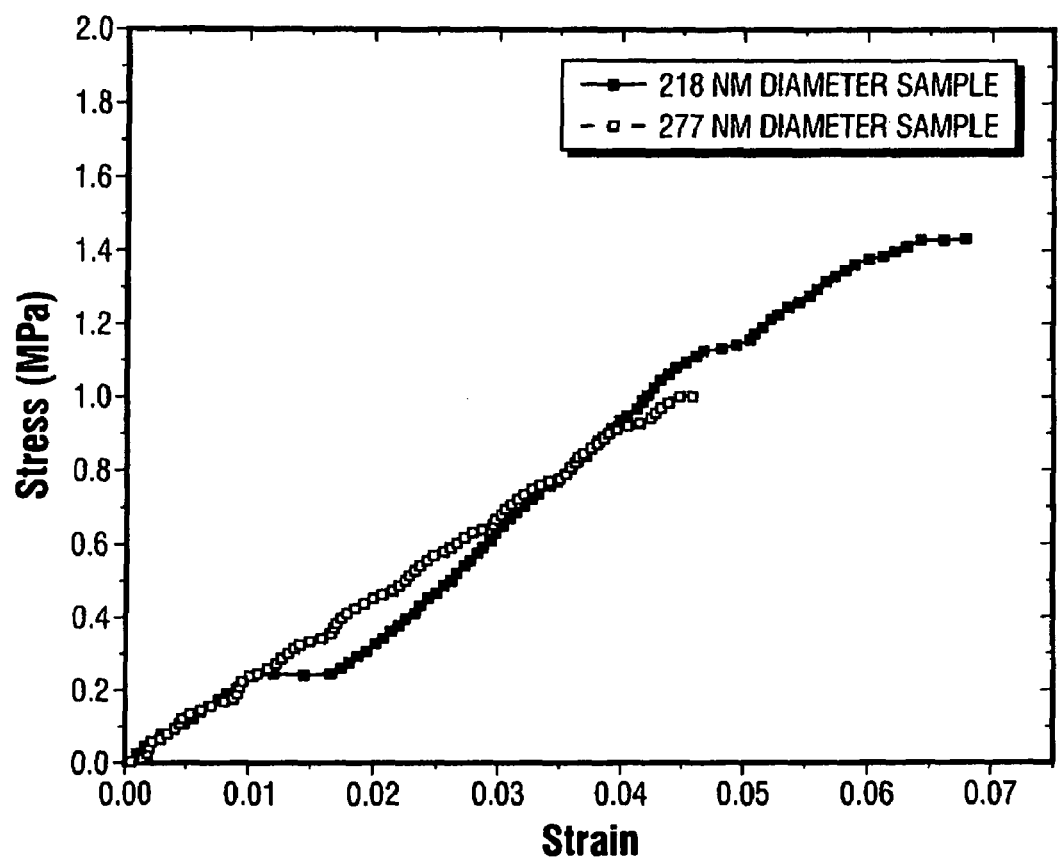
FIG. 10 shows illustrative derived stress vs. strain curves for Ni nanowires having diameters of 277 and 218 nm.

FIG. 8 presents an illustrative plot of nanoindenter load versus displacement for tensile measurement of a Ni nanowire sample. As shown in FIG. 8, the curve exhibited two regions, each having a distinct slope. The slopes of both portions of the curve were used to determine stiffness (i.e., Young's modulus) of the system in the presence and in the absence of a mounted Ni nanowire sample. The initial slope (417 N/m) at small displacements corresponds to the system stiffness in the presence of a mounted Ni nanowire. FIGS. 9A-9F present illustrative time-lapse SEM images of a Ni nanowire mounted to the micromechanical device (t=0 s; t=1 s; t=2 s; t=3 s; t=5 s and t=16 s, respectively), which were obtained while a load was being applied. As verified using the SEM images of FIGS. 9E and 9F, the abrupt change in slope seen in FIG. 8 correlated with failure of the sample. Following sample failure, the slope of the curve at higher displacement values decreased to 126 N/m, which represents the device stiffness alone in the absence of a mounted sample. By interpolation of the slope values, the sample's Young's modulus was determined. FIG. 10 presents illustrative derived stress vs. strain curves for Ni nanowires having diameters of 277 and 218 nm. From the stress vs. strain curves shown in FIG. 10, the Young's modulus for each Ni nanowire sample was determined to be 31.4 and 23.3 GPa, respectively. These values are considerably lower than that of single crystal Ni along the [112] direction (232.5 GPa).

Another feature of the Ni nanowires that was revealed in the measurement was that the nanowires remained elastic and did not fracture until the applied stress reached 1.44 and 1.01 GPa, respectively, for the two diameters (failure strain=6.76 and 4.55% respectively). Such values of failure stress are much higher than those observed in bulk Ni (140-195 MPa). This phenomenon is attributed to the fact that when materials are scaled to nanoscale levels, their strength increases and tends to approach the theoretical strength of the material (viz. $\sim 1/10^{th}$ of the Young's modulus).

Example 4

Testing of Copper Nanorings

Figure 11A:
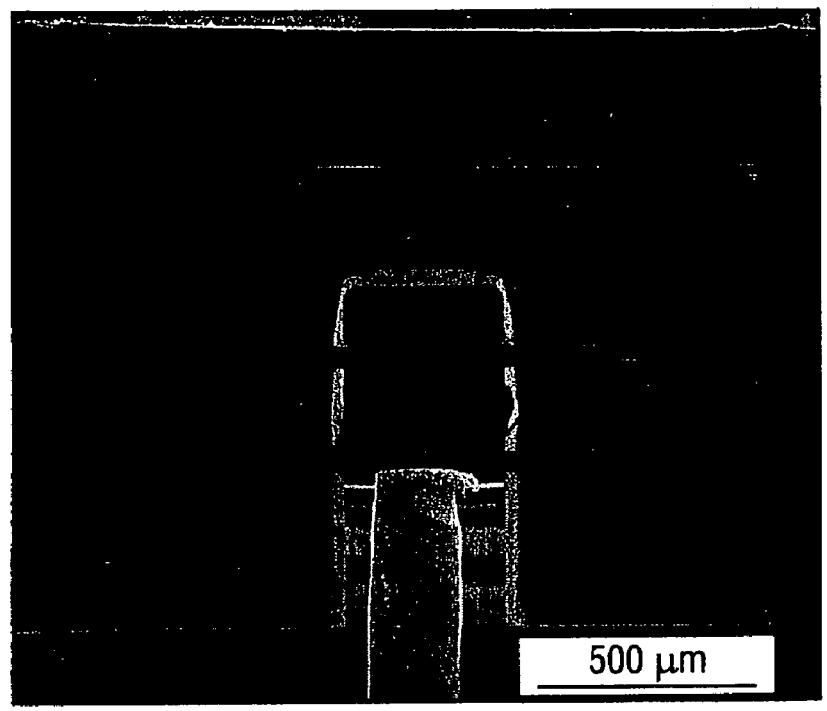
FIGS. 11A and 11B show illustrative SEM images of a copper nanoring being tested using the micromechanical devices described herein.
Figure 11B:
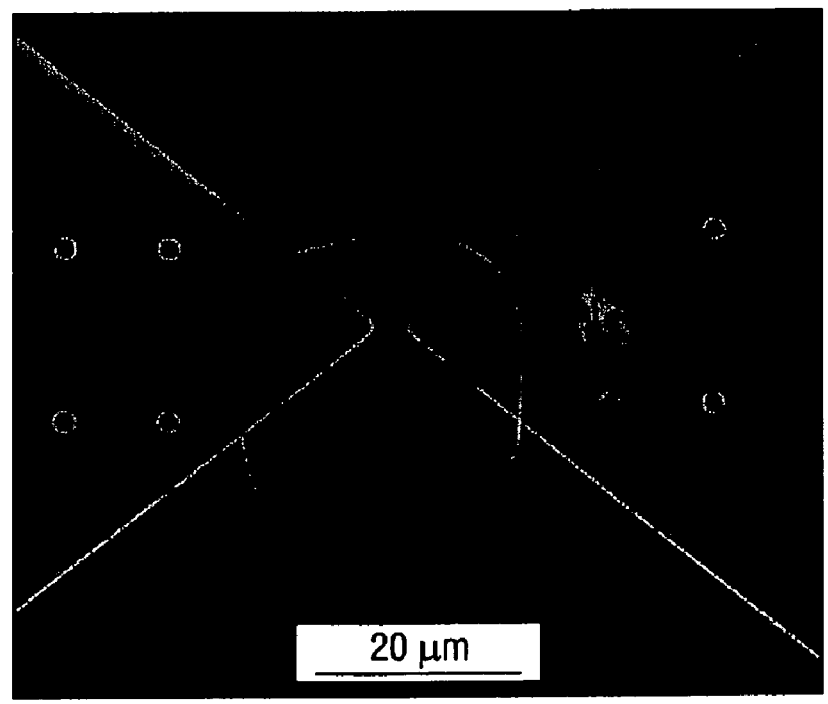

FIGS. 11A and 11B present illustrative SEM images of a copper nanoring being tested using the micromechanical devices described herein. Testing revealed that the stiffness of the copper nanoring was ~2300N/m.

Example 5

Testing of Carbon Nanotubes

Figure 12:
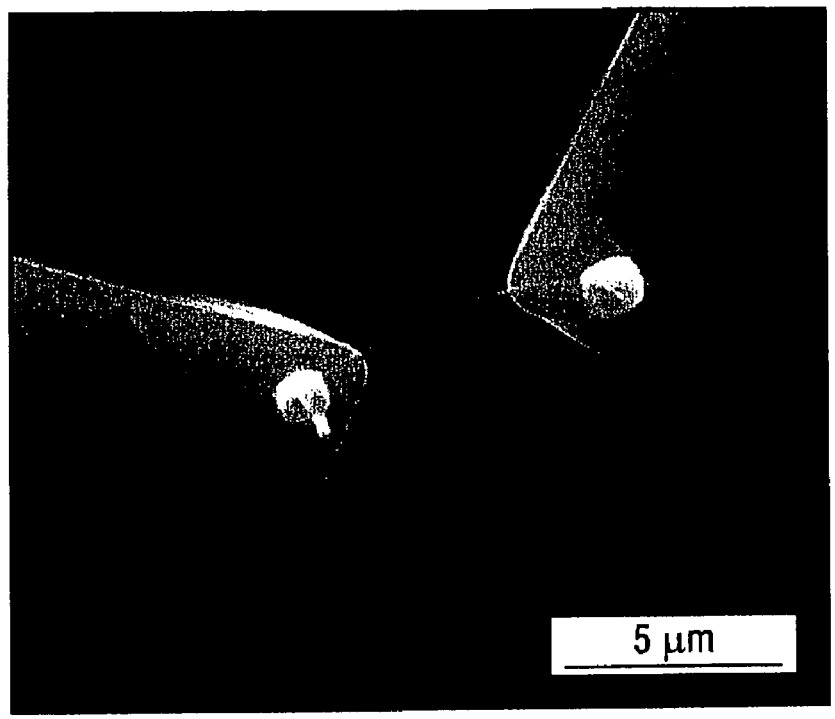
FIG. 12 shows an illustrative SEM image of a carbon nanotube being testing using the micromechanical devices described herein.
Figure 13:
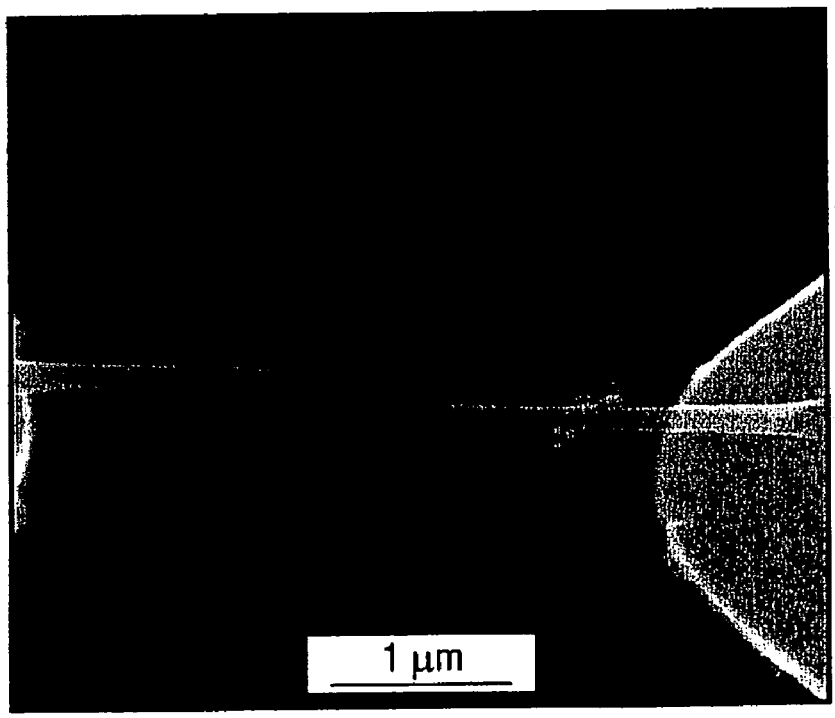
FIG. 13 shows an illustrative SEM image of a fractured carbon nanotube attached to the micromechanical device after tensile failure.

FIG. 12 presents an illustrative SEM image of a carbon nanotube being testing using the micromechanical devices described herein. The Young's modulus and tensile strength of the carbon nanotube were found to be 550 GPa and 10.74 GPa, respectively. FIG. 13 presents an illustrative SEM image of a fractured carbon nanotube attached to the micromechanical device after tensile failure.

Example 6

Testing of Copper Nanowires

Figure 14:
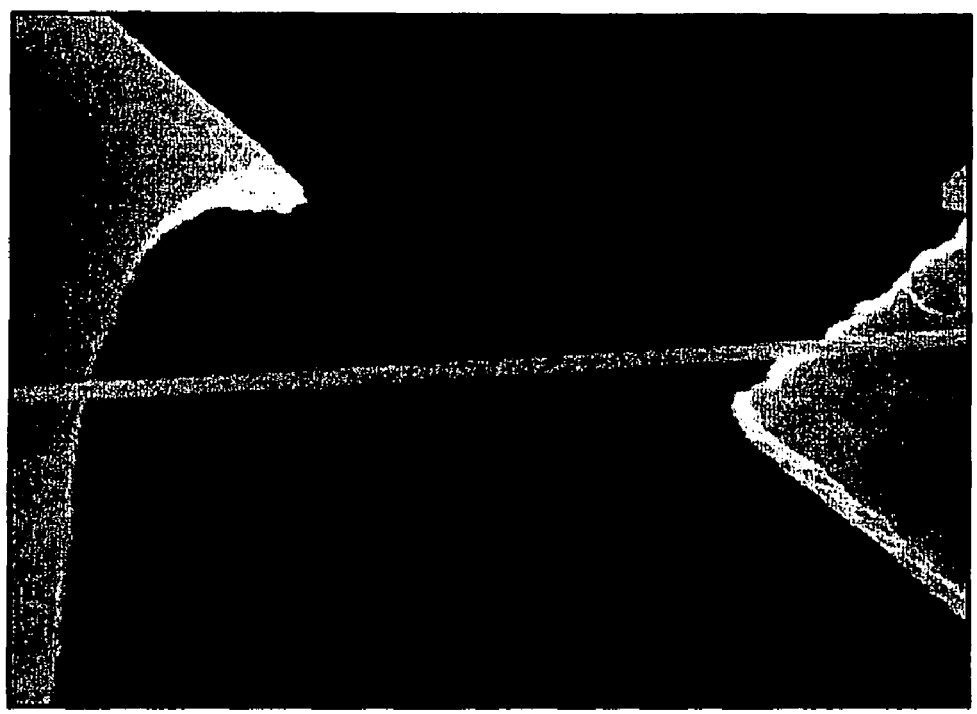
FIG. 14 shows an illustrative SEM image of a copper nanowire being tested using the micromechanical devices described herein.
Figure 15:
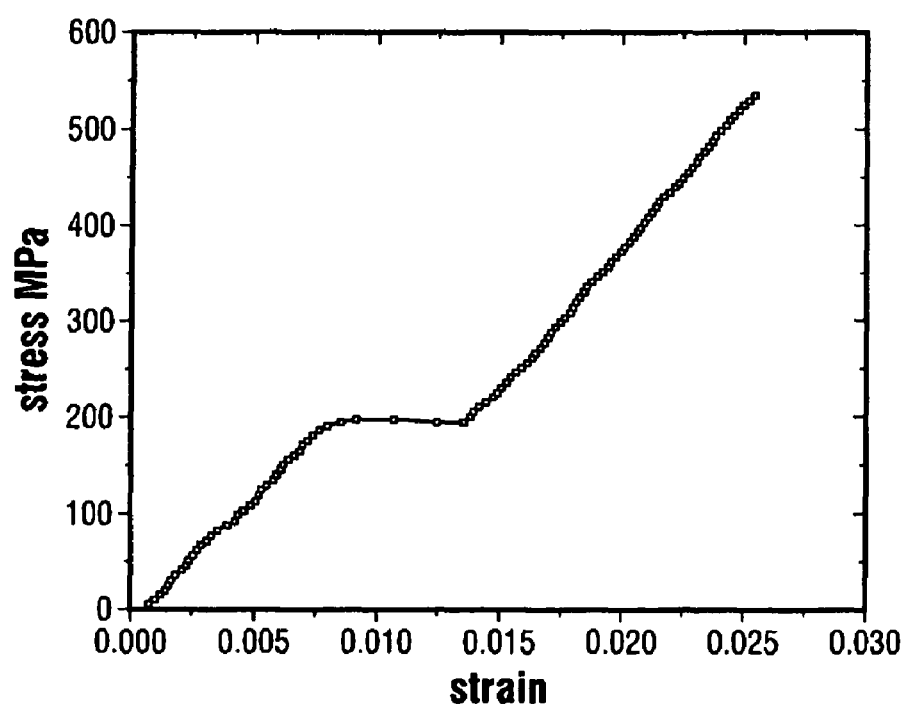
FIG. 15 shows an illustrative stress vs. strain curve derived for the copper nanowire.

FIG. 14 presents an illustrative SEM image of a copper nanowire being tested using the micromechanical devices described herein. FIG. 15 presents an illustrative stress vs. strain curve derived for the copper nanowire.

Example 7

Fiber Pullout Tests from an Epoxy Matrix

Figure 16A:
FIGS. 16A and 16B show illustrative SEM images of a carbon nanotube/epoxy polymer composite being tested using the micromechanical devices described herein, both before and after carbon nanotube pullout.
Figure 16B:
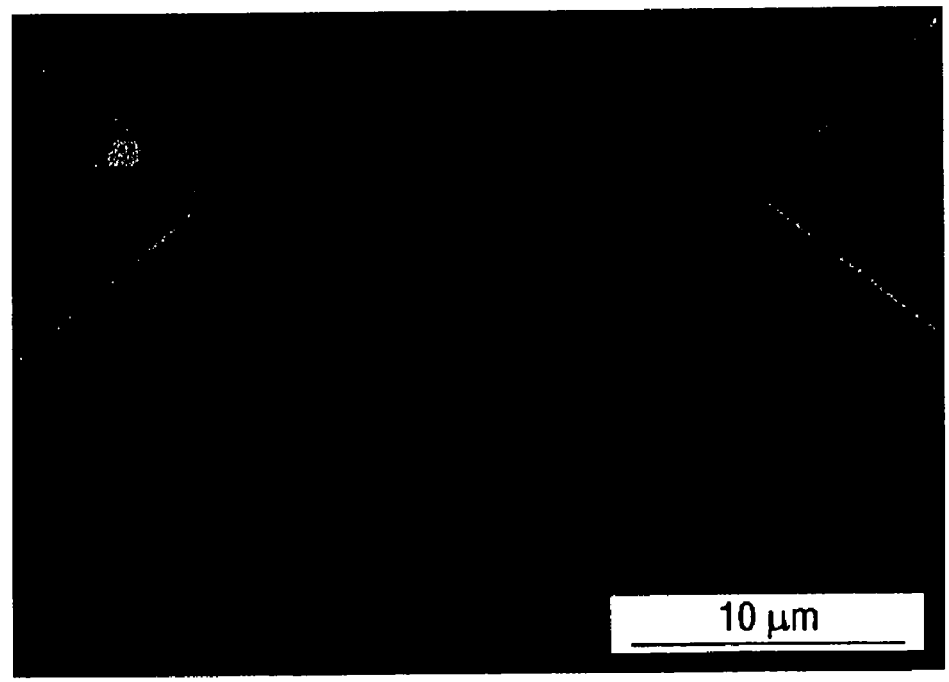

FIGS. 16A and 16B present illustrative SEM images of a carbon nanotube/epoxy polymer composite being tested using the micromechanical devices described herein, both before and after carbon nanotube pullout. As shown in FIG. 16A, one of the sample stage shuttles was coated with epoxy to form the composite, and the carbon nanotube was connected to the other sample stage shuttle. FIG. 16B shows failure of the composite after carbon nanotube pullout. The carbon nanotube and the epoxy remained attached to their respective sample stage shuttles. Testing revealed that the fiber pullout force was 4.4 mN, and interfacial shear stress was found to be 7.3 GPa.

Example 8

Testing of Protein Nanofibrils

The devices described herein may be used to test the strength of protein nanofibrils. In the present example, the devices were used to test the strength of Ubx protein nanofibrils in a device contained in a scanning electron microscope. The protein nanofibrils were not in solution in this example. The protein nanofibrils may also be studied in their native liquid environment by substituting an optical microscope for the scanning electron microscope and immersing the micromechanical device in solution.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

The invention claimed is:

1. A micromechanical device for characterizing a material's strength, said device comprising:
 an anchor pad;
 a top shuttle platform;
 a nanoindenter in movable contact with the top shuttle platform;
  wherein the nanoindenter applies a compression force to the top shuttle platform; and
 at least two sample stage shuttles;
  wherein each of the at least two sample stage shuttles is connected to the top shuttle platform by at least one inclined beam;
  wherein each of the at least two sample stage shuttles is connected to the anchor pad by at least one inclined beam; and
  wherein the at least two sample stage shuttles move apart from one another in response to the compression force.

2. The device of claim 1, further comprising:
 a viewing means for observing a material in the device while the compression force is being applied.

3. The device of claim 2, wherein the viewing means is a transmission electron microscope.

4. The device of claim 2, wherein the viewing means is a scanning electron microscope.

5. The device of claim 2, wherein the viewing means is an optical microscope.

6. The device of claim 2, further comprising:
 a viewing window that is substantially transparent to the viewing means.

7. The device of claim 1, wherein there are equal numbers of inclined beams on each sample stage shuttle.

8. The device of claim 7, wherein there are two planes of symmetry bisecting the device.

9. The device of claim 1, wherein there are equal numbers of inclined beams connecting each sample stage shuttle to the top shuttle platform and to the anchor pad.

10. The device of claim 1, wherein there is an asymmetrical placement of the inclined beams on the sample stage shuttles.

11. The device of claim 1, wherein there are unequal numbers of inclined beams connecting each sample stage shuttle to the top shuttle platform and to the anchor pad.

12. The device of claim 11, wherein there are two planes of symmetry bisecting the device.

13. The device of claim 1, wherein each inclined beam contacts the at least two sample stage shuttles at the same angle.

14. The device of claim 1, wherein at least one of the inclined beams contacts the at least two sample stage shuttles at an angle that is different than that of any other of the inclined beams.

15. The device of claim 1, wherein a stiffness of the device is adjustable by modifying at least one device parameter selected from the group consisting of a thickness of the device, a number of inclined beams, and an angle at which the inclined beams contact the at least two sample stage shuttles.

16. The device of claim 1, wherein the nanoindenter is a quantitative nanoindenter.

17. The device of claim 1, wherein the nanoindenter comprises a blunt cube corner nanoindenter tip.

18. The device of claim 1, wherein the device comprises silicon.

19. A method for measuring a sample's strength, said method comprising:
 providing the device of claim 1;
 connecting a sample between the at least two sample stage shuttles;
 applying a compression force to the top shuttle platform with the nanoindenter; and
 measuring a tip displacement of the nanoindenter.

20. The method of claim 19, wherein the tip displacement correlates with the sample's strength.

21. The method of claim 19, further comprising:
 placing the device on a stage of a microscope.

22. The method of claim 21, further comprising:
 observing the sample with the microscope while the compression force is being applied.

23. The method of claim 22, wherein the microscope is selected from the group consisting of a scanning electron microscope and a transmission electron microscope.

24. The method of claim 23, wherein the observing step is conducted with an electron beam.

25. The method of claim 22, wherein the microscope is an optical microscope.

26. The method of claim 25, wherein the device is immersed in a liquid.

27. The method of claim 19, wherein the connecting step comprises attaching the sample to the at least two sample stage shuttles with epoxy.

* * * * *